United States Patent
Farri et al.

(10) Patent No.: US 11,403,786 B2
(45) Date of Patent: Aug. 2, 2022

(54) METHOD AND SYSTEM FOR GENERATING MEDICAL IMAGE BASED ON TEXTUAL DATA IN MEDICAL REPORT

(71) Applicant: KONINKLIJKE PHILIPS N.V., Eindhoven (NL)

(72) Inventors: Oladimeji Feyisetan Farri, Yorktown Heights, NY (US); Rithesh Sreenivasan, Bangalore (IN); Vikram Basawaraj Patil Okaly, Bangalore (IN); Ravindra Balasaheb Patil, Bangalore (IN); Krishnamoorthy Palanisamy, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 16/980,935

(22) PCT Filed: Mar. 15, 2019

(86) PCT No.: PCT/EP2019/056577
§ 371 (c)(1),
(2) Date: Sep. 15, 2020

(87) PCT Pub. No.: WO2019/175404
PCT Pub. Date: Sep. 19, 2019

(65) Prior Publication Data
US 2020/0410721 A1    Dec. 31, 2020

Related U.S. Application Data

(60) Provisional application No. 62/643,816, filed on Mar. 16, 2018.

(51) Int. Cl.
*G06T 11/00* (2006.01)
*G16H 15/00* (2018.01)
(Continued)

(52) U.S. Cl.
CPC ............. *G06T 11/00* (2013.01); *G06F 40/289* (2020.01); *G16H 15/00* (2018.01); *G16H 30/20* (2018.01);
(Continued)

(58) Field of Classification Search
CPC ... G06T 11/00; G06T 2210/41; G06F 40/289; G16H 15/00; G16H 30/20; G16H 30/40; G16H 50/20; G16H 50/70
(Continued)

(56) References Cited

U.S. PATENT DOCUMENTS

| 2016/0350919 | A1 | 12/2016 | Steigauf |
| 2016/0361025 | A1* | 12/2016 | Reicher ............... A61B 5/7267 |
| 2018/0068076 | A1 | 3/2018 | Farri |

FOREIGN PATENT DOCUMENTS

| WO | 2017/151757 | 9/2017 | |
| WO | WO-2017151757 A1 * | 9/2017 | ........... G06N 3/0454 |

OTHER PUBLICATIONS

International Search Report and Written Opinion dated May 27, 2019 for International Application No. PCT/EP2019/056577 Filed Mar. 15, 2019.
(Continued)

*Primary Examiner* — Jennifer Mehmood
*Assistant Examiner* — Kim Thanh T Tran

(57) ABSTRACT

Embodiments of present disclosure disclose method and system for generating a medical image based on a textual data in a medical report. For generation, a textual data from each of one or more medical reports of the patient is retrieved. The textual data comprises one or more medical events and corresponding one or more attributes associated with each of the one or more medical reports. Further, a matching score for each of plurality of reference images is computed based on the textual data, using a first machine
(Continued)

learning model. Upon computing the matching score, one or more images are selected from the plurality of reference images based on the matching score associated with each of the plurality of reference images. The medical image for the patient is generated based on the one or more images and the textual data using a second machine learning model.

20 Claims, 6 Drawing Sheets

(51) Int. Cl.
*G16H 30/20* (2018.01)
*G16H 50/70* (2018.01)
*G16H 50/20* (2018.01)
*G16H 30/40* (2018.01)
*G06F 40/289* (2020.01)

(52) U.S. Cl.
CPC ............. *G16H 30/40* (2018.01); *G16H 50/20* (2018.01); *G16H 50/70* (2018.01); *G06T 2210/41* (2013.01)

(58) Field of Classification Search
USPC .......................................................... 345/619
See application file for complete search history.

(56) References Cited

OTHER PUBLICATIONS

Zhang, et al: "StackGAN: Text to Photo-realistic Image Synthesis with Stacked Generative Adversarial Networks", arxiv.org, Cornell University Library, Dec. 10, 2016.
Tan, et al: "phi-LSTM: A Phrase-Based Hierarchical LSTM Model for Image Captioning", Springer International Publishing, AG 2017.
Miao, Et Al.: "Deep Captioning With Multimodal Recurrent Neural Networks (M-Rnn)", Published as a conference paper at ICLR 2015.
Shin, Et Al: "Interleaved Text/Image Deep Mining on a Large-Scale Radiology Database for Automated Image Interpretation". Journal of Machine Learning Research (2015).
Krizhevsky, et al: "ImageNet Classification with Deep Convolutional Neural Networks", Advances in Neural Information Processing Systems 25 (NIPS 2012).

* cited by examiner

METHOD AND SYSTEM FOR GENERATING MEDICAL IMAGE BASED ON TEXTUAL DATA IN MEDICAL REPORT

CROSS REFERENCE TO RELATED APPLICATIONS

This application is the U.S. National Phase application under 35 U.S.C. § 371 of International Application No. PCT/EP2019/056577 filed Mar. 15, 2019, which claims the benefit of U.S. Provisional Patent Application No. 62/643,816 filed Mar. 16, 2018. These applications are hereby incorporated by reference herein.

TECHNICAL FIELD

The present subject matter is related in general to field of healthcare, more particularly, but not exclusively to a system and method for generating a medical image based on textual data in a medical report of a patient.

BACKGROUND

Radiology Information Systems (RIS) in medical institutes such as speciality hospitals, sub-speciality hospitals, diagnostic centres and so on, may be configured to manage medical data associated with every patient relating to the medical institutes. The medical data may include data associated with patient administration, examination, reporting, statistics, system administration so on. Medical data managed by the RIS may be used for several purposes such as displaying, storing, retrieving, transferring, exchanging, printing orders, results, reports, and so on. However, deployment of the RIS in a medical institute is a complex procedure. Also, there may be some medical institutes which may not be able to afford such manging systems. Typically, after an examination which may be a Computed Tomography (CT) scan, Magnetic Resonance Imaging (MRI) scan, Echocardiogram (ECG) and so on, only text report associated with the examination may be provided to the patient. Images generated upon the examination may be archived by the medical institutes and not be provided to the patient. Also, there are possibilities that the generated images may be rendered unusable due to mishandling or may be misplaced. For an examiner, who may be doctor or a physician, analysing state of a patient based on only text reports may be difficult. Even a follow-up consultation of the patient may be difficult with mere text reports.

The information disclosed in this background of the disclosure section is only for enhancement of understanding of the general background of the invention and should not be taken as an acknowledgement or any form of suggestion that this information forms the prior art already known to a person skilled in the art.

SUMMARY

In an embodiment, the present disclosure relates to a method for generating a medical image based on textual data in a medical report of a patient. Initially, for the generation, a textual data from each of one or more medical reports of the patient is retrieved. The textual data comprises one or more medical events and corresponding one or more attributes associated with each of the one or more medical reports. Further, a matching score for each of plurality of reference images is computed based on the textual data, using a first machine learning model. Upon computing the matching score, one or more images are selected from the plurality of reference images based on the matching score associated with each of the plurality of reference images. The medical image for the patient is generated based on the one or more images and the textual data using a second machine learning model.

In an embodiment, the present disclosure relates to an image generation system for generating a medical image based on textual data in a medical report of a patient. The image generation system comprises a processor and a memory communicatively coupled to the processor. The memory stores processor-executable instructions which on execution cause the processor to generate the medical image. Initially, for the generation, a textual data from each of one or more medical reports of the patient is retrieved. The textual data comprises one or more medical events and corresponding one or more attributes associated with each of the one or more medical reports. Further, a matching score for each of plurality of reference images is computed based on the textual data, using a first machine learning model. Upon computing the matching score, one or more images are selected from the plurality of reference images based on the matching score associated with each of the plurality of reference images. The medical image for the patient is generated based on the one or more images and the textual data using a second machine learning model.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and regarding the accompanying figures, in which:

Figure 1:
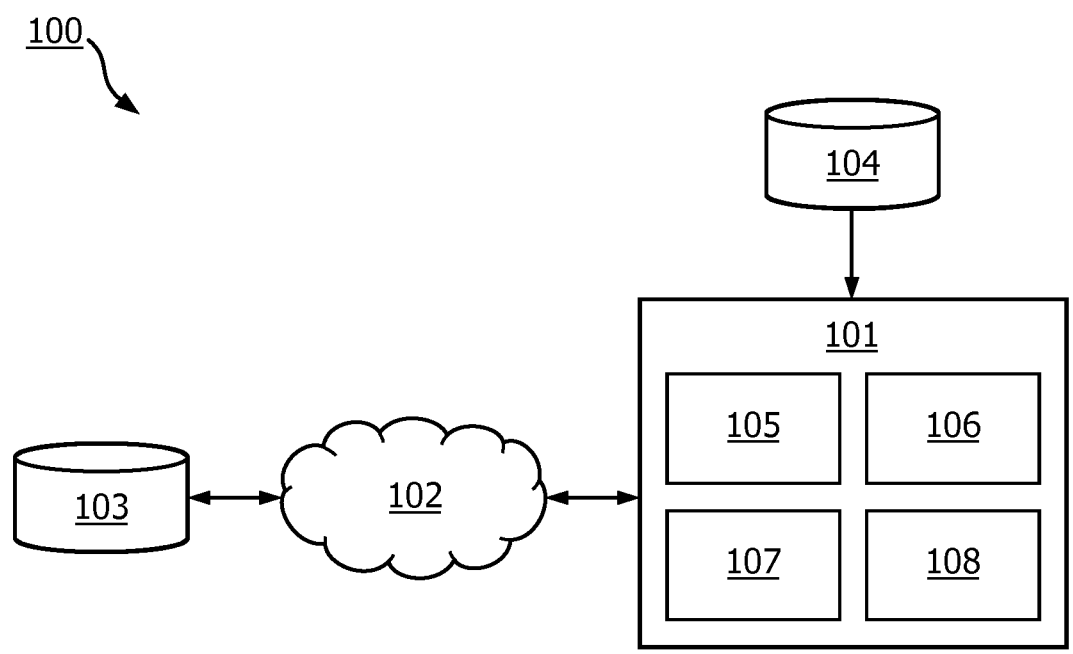
FIG. 1 illustrates an exemplary health care system for generating a medical image based on textual data in a medical report of a patient, in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The terms "includes", "including", or any other variations thereof, are intended to cover a non-exclusive inclusion, such that a setup, device or method that includes a list of components or steps does not include only those components or steps but may include other components or steps not expressly listed or inherent to such setup or device or method. In other words, one or more elements in a system or apparatus proceeded by "includes . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Present disclosure provides an efficient methodology for evaluation of health status of a patient by generating a medical image based on textual data in a medical report. The present disclosure leverages a deep learning architecture to extract medical events and their attributes from one or more medical reports and synthesizes a composite medical image highlighting details on the health status, visually. System disclosed in the present disclosure implements machine learning models for generating the medical image. Based on the textual data, a matching score for each of plurality of reference images is computed using a first machine learning model. Further, one or more images from the plurality of reference images are selected based on the matching score. Using a second machine learning model, the medical image may be generated based on the selected one or more images. By the generated medical image, ability to visualize the health status of the patient may be achieved.

FIG. 1 illustrates an exemplary health care system 100 comprising an image generation system 101 for generating a medical image based on textual data in a medical report. The exemplary health care system 100 may comprise the image generation system 101, a communication network 102, a medical report repository 103 and a reference image repository 104, to generate the medical image. The image generation system 101 may be configured to generate the medical image by performing steps as disclosed in the present disclosure. The image generation system 101 may communicate with the medical report repository 103 via the communication network 102 as shown in the figure. One or more medical reports associated with a patient may be retrieved from the medical report repository 103 by the image generation system 101 via the communication network 102, for generating the medical image for the patient. The patient may be any person whose health status needs to be evaluated by a doctor or a physician or any other person who may be capable to evaluate the health status. In an embodiment, the medical report repository 103 may be a storage space configured to store the one or more medical reports of a patient. In an embodiment, the medical report repository 103 may be associated with at least one of a user device associated with the patient, a medical institute related to the patient and a third party configured to store the one or more medical reports. In an embodiment, the medical report repository 103 may be a cloud system configured to receive and store the one or more medical reports and provide the one or more medical reports to the image generation system 101 for generating the medical image. The reference image repository 104 is configured to store plurality of reference images. The plurality of reference images are images relating to radiology examination. The radiology examination may be associated with one or more modalities which may include, but are not limited to, CT scan, MRI scan, ECG and so on. The reference image repository 104 may be associated with the medical institutes. In an embodiment, the reference image repository may be configured to retrieve the plurality of reference images, dynamically, from radiology systems associated with the medical institutes. The image generation system 101 may retrieve the plurality of reference images from the reference image repository 104, for generating the medical image. In an embodiment, the image generation system 101 may communicate with the reference image repository 104 via the communication network 102 to retrieve the plurality of reference images (not shown in figure). In an embodiment, the medical report repository 103 and the reference image repository 104 may be integrated within the image generation system 101. In an embodiment, the communication network 102 may include, without limitation, a direct interconnection, Local Area Network (LAN), Wide Area Network (WAN), wireless network (e.g., using Wireless Application Protocol), the Internet, and the like.

Further, the image generation system 101 may include a processor 105, a I/O interface 106, one or more modules 107 and a memory 108. In some embodiments, the memory 108 may be communicatively coupled to the processor 105. The memory 108 stores processor executable instructions, which, on execution, may cause the image generation system 101 to generate the medical image, as disclosed in the present disclosure. The image generation system 101 may be implemented in a variety of computing systems, such as a laptop computer, a desktop computer, a Personal Computer (PC), a notebook, a smartphone, a tablet, e-book readers, a server, a network server, and the like.

For generating the medical report, initially, a textual data from each of the one or more medical reports of the patient from the medical report repository 103 may be retrieved. The textual data may comprise one or more medical events and corresponding one or more attributes associated with each of the one or more medical reports. The one or more attributes, corresponding to each of the one or more medical events, may comprise a date attribute, a time attribute, a modality attribute, a qualitative attribute, and a quantitative attribute associated with corresponding medical event. In an embodiment, the one or more medical events and the corresponding one or more attributes may be arranged in a chronological order, in the textual data.

Upon retrieving the textual data, a matching score for each of the plurality of reference images from the reference image repository 104, is computed based on the textual data. The matching score may be computed using a first machine learning model. The matching score may be computed by generating a vector representation for each of the plurality of reference images. Based on the corresponding vector representation and the textual data, a joint vector representation for each of the plurality of reference images may be generated. Based on the joint vector representation of respective reference image, the matching score is computed for each of the plurality of reference images. In an embodiment, the first machine learning model may be a multimodal Convolution Neural Network (CNN).

Upon computing the matching score, one or more images are selected from the plurality of reference images based on the matching score associated with each of the plurality of reference images. In an embodiment, the matching score of each of the plurality of images may be compared with a predefined matching score. The one or more images from the plurality of reference images, associated with the matching score greater than the predefined matching score may be selected from the plurality of reference images. In an embodiment, the one or more images may be associated with higher values of the matching score. For example, the one or more images with top ten values of the matching score may be selected from the plurality of images. One or more techniques, known to a person skilled in the art, may be used for selected the one or more images from the plurality of reference images.

Further, upon selection of the one or more images, a second machine learning model may be implemented for generating the medical image for the patient. The medical image may be generated based on the one or more images and the textual data. For generation of the medical image, initially, a first sequence comprising vector representation of one of words and phrases in the textual data may be retrieved. For retrieving the first sequence, backward hidden states and forward hidden states associated with one of the words and the phrases in textual data may be determined. The backward hidden states may be determined using backward Long Short-Term Memory (LSTM) unit and the forward hidden states may be determined using forward LSTM unit, respectively. Further, the backward hidden states and the forward hidden states may be concatenated for retrieving the first sequence.

Upon retrieving the first sequence, a second sequence comprising the one or more images, selected from the plurality of images, may be retrieved. A medical event image may be generated for each of the one or more medical events of the textual data, based on the first sequence and the second sequence. In an embodiment, the medical event image may be generated to represent the health status of the patient based on the corresponding medical event. Upon generating the medical event image for each of the one or more medical events, the medical event image for each of the one or more medical events is stitched for generating the medical image. In an embodiment, the medical event image for each of the one or more medical events may be stitched in a predefined pattern. In an embodiment, the predefined pattern may be selected based on the chronological order associated with the one or more medical events.

In an embodiment, the second machine learning model may be trained to generate the medical image based on the plurality of reference images and a predefined textual data. In an embodiment, the one or more images selected from the plurality of reference images may also be used to train the second machine learning model, dynamically. In an embodiment, the second machine learning model may be a Recurrent Neural Network (RNN) model.

Figure 2:
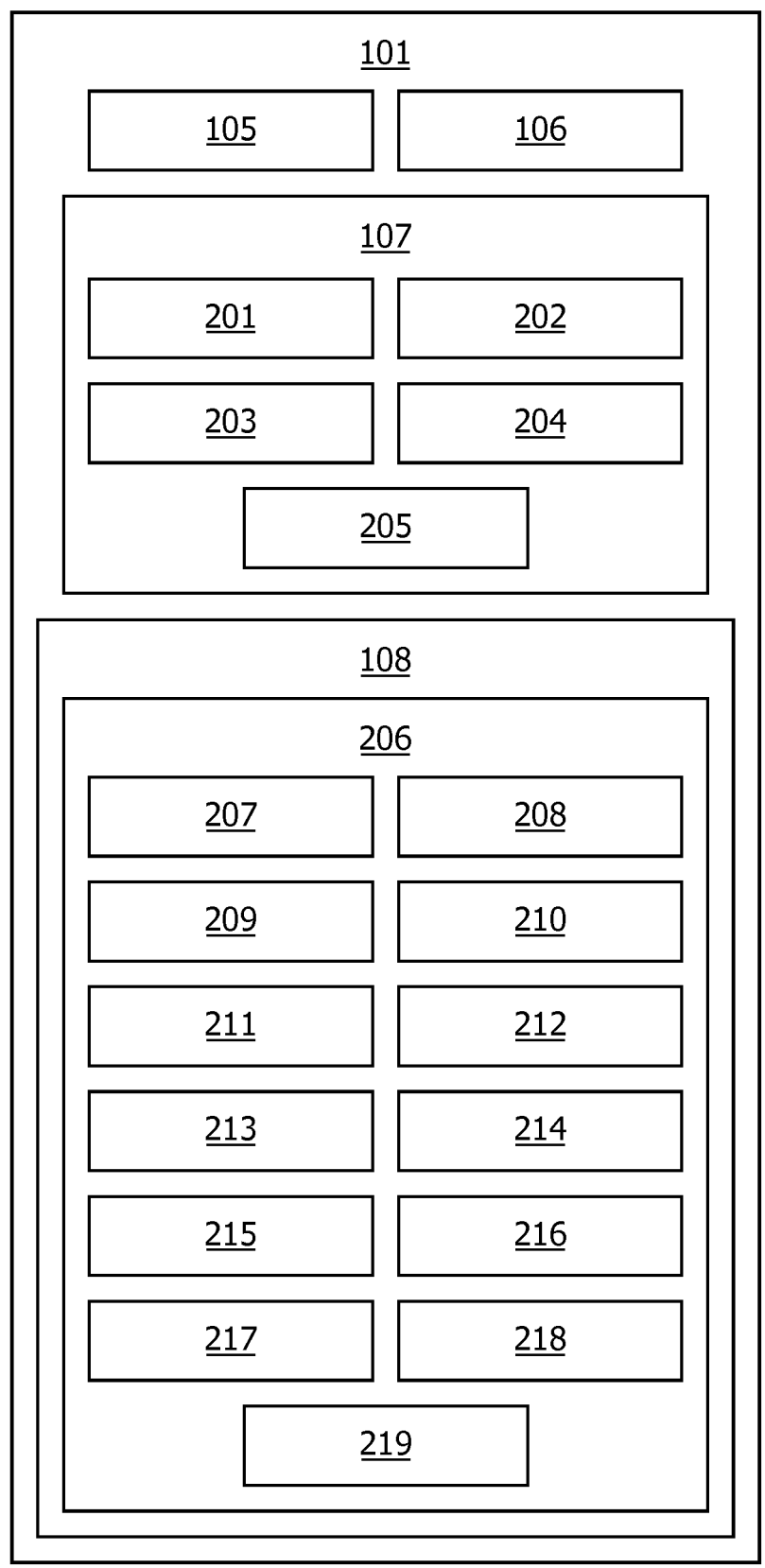
FIG. 2 shows a detailed block diagram of an image generation system for generating a medical image based on textual data in a medical report of a patient, in accordance with some embodiments of the present disclosure.

FIG. 2 shows a detailed block diagram of the image generation system 101 for generating the medical image in accordance with some embodiments of the present disclosure.

Data 206 in the memory 108 and the one or more modules 107 of the image generation system 101 may be described herein in detail.

In one implementation, the one or more modules 107 may include, but are not limited to, a textual data retrieve module 201, a matching score computation module 202, an image selection module 203, a medical image generation module 204, and one or more other modules 205, associated with the image generation system 101.

In an embodiment, the data 206 in the memory 108 may comprise medical report data 207 (also referred to as one or more medical reports 207), textual data 208, matching score 209, reference image data 210 (also referred to as plurality of reference images 210), vector representation data 211 (also referred to as vector representation 211), joint vector representation data 212 (also referred to as joint vector representation 212), first sequence data 213 (also referred to as first sequence 213), second sequence data 214 (also referred to as second sequence 214), medical event image data 215 (also referred to as medical event image 215), backward hidden state data 216 (also referred to as backward hidden states 216), forward hidden state data 217 (also referred to as forward hidden states 217), medical image data 218 (also referred to as medical image 218), and other data 219 associated with the image generation system 101.

In an embodiment, the data 206 in the memory 108 may be processed by the one or more modules 107 of the image generation system 101. As used herein, the term module refers to an Application Specific Integrated Circuit (ASIC), an electronic circuit, a Field-Programmable Gate Arrays (FPGA), Programmable System-on-Chip (PSoC), a combinational logic circuit, and/or other suitable components that provide the described functionality. The one or more modules 107 when configured with the functionality defined in the present disclosure may result in a novel hardware.

The textual data 208 retrieved, by the textual data retrieve module 201, from each of the one or more medical reports 207 of a patient may comprise the one or more medical events and corresponding one or more attributes associated with each of the one or more medical reports 207. For retrieving the textual data 208, the textual data retrieve module 201 may be configured to process the one or more medical reports 207 using Natural Language Processing (NLP). By the NLP, stop word removal, sentence detection and ontology look-up and so on may be performed on the one or more medical reports 207. In an embodiment, for the NLP, the textual data retrieve module 201 may use medical ontologies such as Systematized Nomenclature of Medicine Clinical Terms (SNOMED CT) and other such dictionaries within Unified Medical Language System (UMLS). In an embodiment, by the NLP, annotation and extraction of entities such as anatomical locations, clinical signs and symptoms, temporality i.e., time expressions, laterality, and correlations associated with the one or more medical reports 207 may be performed. Further, upon preforming NLP, the textual data retrieve module 201 may implement an extraction module to organize the one or more medical events and the corresponding one or more attributes in the chronological order. In an embodiment, each of the one or more medical events may correspond to a medical report from the one or more medical reports 207. In an embodiment, the one or more attributes may comprise the date attribute, the time attribute, the modality attribute, the qualitative attribute, and the quantitative attribute associated with corresponding medical event. An exemplary example for the textual data 208 retrieved by the textual data retrieve module 201 may be shown in Table 1 given below:

TABLE 1

| Date attribute | Time attribute | Modality attribute | Qualitative attribute | Quantitative attribute |
|---|---|---|---|---|
| 15-02-2010 | 11:30:00 | Angiogram | Increased stenosis in LAD proximal | 90% |
| 19-05-2011 | 12:49:00 | Angiogram | Stenosis in LAD proximal | 70% |
| 15-04-2012 | 11:36:20 | Angiogram | Stenosis in LAD proximal | 45% |
| 15-04-2013 | 01:33:00 | Angiogram | Decreased stenosis in LAD proximal | 10% |

In the textual data 208 illustrated in Table 1, each row in the table represents a medical event and hence the textual data 208 comprises four medical events. Each row may correspond to a medical report of the patient. Every column in the table indicates an attribute from the one or more attribute. The date attribute may indicate date on which the medical event was recorded in the medical report. The time attribute may indicate time at which the medical event was recorded in the medical report. The modality attribute may indicate field of radiology associated with the medical report. For example, the field of radiology may include, but is not limited to, CT, MRI, ECG, angiogram and so on. The qualitative attribute may indicate problem associated with the patient. The quantitative attribute may indicate quantity of said problem. For example, consider first row of the textual data 208 illustrated in Table 1. The corresponding medical report was recorded on "15-02-2010" at "11:30:00" and is related to "angiogram" of the patient. The problem that is detected is "Increased stenosis in LAD proximal" and the quantity of the stenosis is "90%".

Upon retrieving the textual data 208, the matching score 209 for each of the plurality of reference images 210 from the reference image repository 104 may be computed by the matching score computation module 201, based on the textual data 208. The matching score 209 may be computed using the first machine learning model. In an embodiment, the first machine learning model may be a multimodal Convolution Neural Network (CNN). In an embodiment, the multimodal CNN may include an image CNN, a matching CNN, and a multilayer perceptron for computing the matching score 209. The image CNN may be used to generate the vector representation 211 for the plurality of reference images 210. In an embodiment, the vector representation 211 may be generated using equation 1, given below:

$$V_{im} = \sigma(w_{im}(CNN_{im}(I)) + b_{im}) \ldots \quad (1)$$

where,

'σ' may be an activation function. For example, σ may be a sigmoid, Rectified Linear Unit (ReLU) and so on;

'CNNim(I)' may be the image CNN which takes each of the plurality of reference images 210 as input i.e., 'I' and generates a fixed length vector representation Vim of the corresponding reference image;

'wim' may be weight matrix; and

'bim' may be bias.

Further, the matching CNN may be used to generate the joint vector representation 212 based on the vector representation 211. The vector representation and the textual data 208 are provided as input to the matching CNN to output the joint vector representation 212.

Further, the multilayer perceptron may be used to compute the matching score 209 for each of the plurality of reference images 210 based on corresponding joint vector representation 212. In an embodiment, the matching score 209 may be computed using equation 2, given below:

$$Sm = ws(\sigma(wh(VJR) + bh)) + bs \ldots \quad (2)$$

where,

'VJR' may be joint vector representation 212;

'Σ' is non-linear activation function;

'wh' and 'bh' are used to map VJR to the representation in hidden layer of the multilayer perceptron; and '$w_s$' and '$b_s$' are used to compute the matching score 209.

Upon computing the matching score 209, the one or more images are selected from the plurality of reference images 210 by the image selection module 203, based on the matching score 209 associated with each of the plurality of reference images 210. In an embodiment, the one or more images may be images that may be relevant to the modality attribute indicated in the textual data 208. In an embodiment, the plurality of reference images 210 may be filtered out based on the one or more attributes in the textual data 208. For example, from the textual data 208 illustrated in Table 1, images relating to angiogram modality may be filtered out from the plurality of reference images 210 and further provided to the image selection module 203 for selecting the one or more images. One or more other techniques, known to a person skilled in the art, may be used for selected the one or more images from the plurality of reference images 210.

Further, upon selection of the one or more images, the medical image generation module 204 may be configured to use the second machine learning model for generating the medical image 218 for the patient. In an embodiment, the second machine learning model may be the RNN model. In an embodiment, the RNN model may include a bidirectional RNN and a generative RNN model for generating the medical image 218. Further, the bidirectional RNN may include the backward LSTM unit and the forward LSTM unit. Using the bidirectional RNN, the first sequence 213 comprising vector representation 211 of one of words and phrases in the textual data 208 may be retrieved.

The backward LSTM unit may be configured to determine the backward hidden states 216 of one of words and phrases in the textual data 208. The forward LSTM unit may be configured to determine the forward hidden states 217 of one of words and phrases in the textual data 208. In an embodiment, the bidirectional RNN may comprises forget gates along with the backward LSTM unit and the forward LSTM unit, to determine the backward hidden states 216 and the forward hidden states 217. In an embodiment, the bidirectional RNN may be an attention-based bidirectional RNN model. Further, the backward hidden states 216 and the forward hidden states 217 may be concatenated to retrieve the first sequence 213. In an embodiment, a soft attention mechanism may be used on the first sequence 213 by maximizing variation lower bound of maximum likelihood. One or more other techniques, known to a person skilled in art may be implemented for retrieving the first sequence 213 of one of the words and the phrases.

Further, the medical image generation module 204 may be configured to retrieve the second sequence 214 comprising the one or more images which are selected from the plurality of images. In an embodiment, the second sequence 214 may be formed by arranging the one or more images as sequence of patches on a canvas, as a function of time. The generative RNN model may be configured to generate the medical event image 215 for each of the one or more medical events of the textual data 208, based on the first sequence 213 and the second sequence 214. In an embodiment, a latent sequence, comprising latent variables, may also be used by the generative RNN for generating the medical event image 215 for each of the one or more medical events. The latent sequence may be used to compute approximate posterior of associated with the first sequence 213 and the second sequence 214 over the latent sequence, for generating the medical event image 215.

Figure 7:
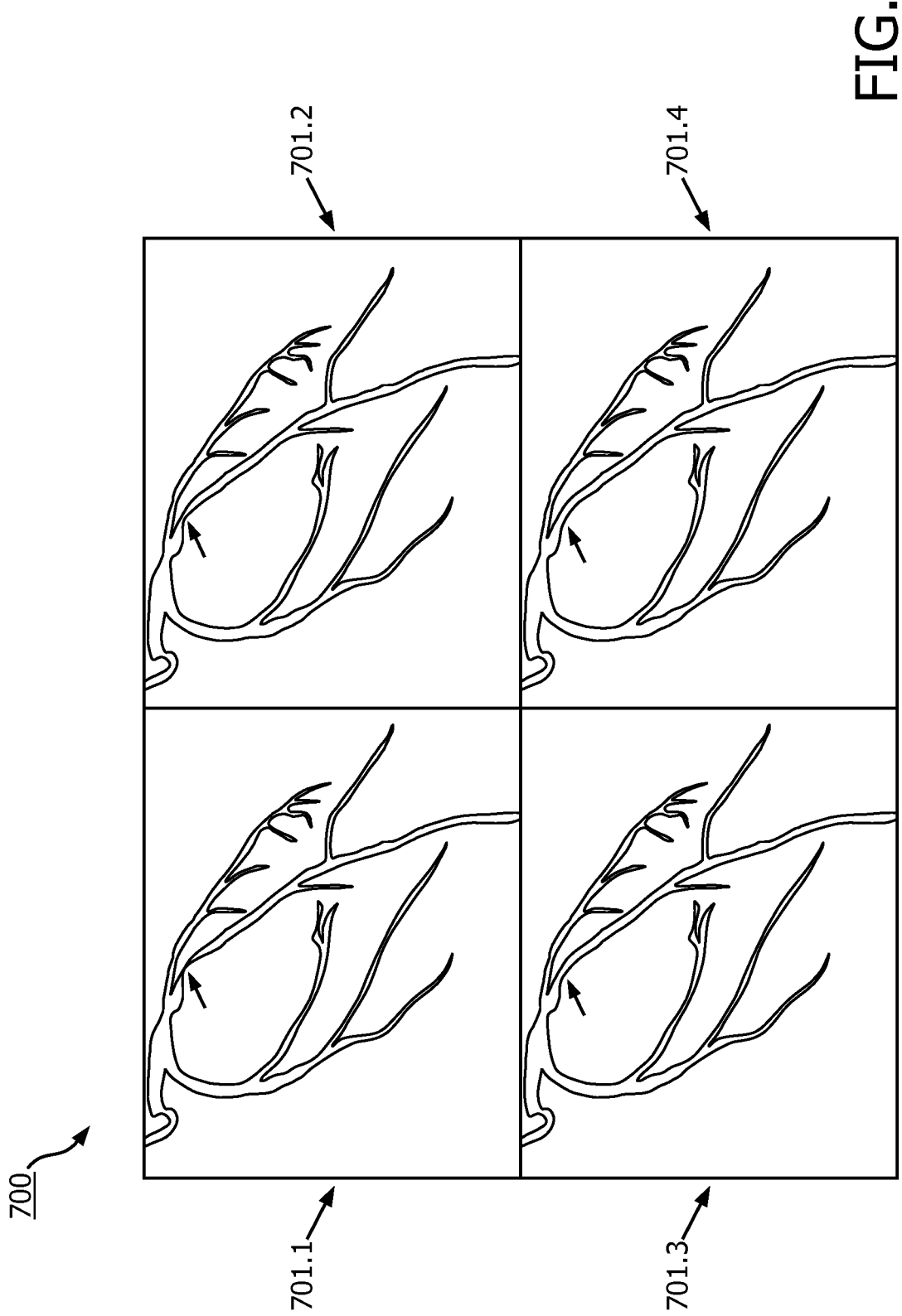
FIG. 7 shows an exemplary representation of a medical image generated in accordance with some embodiments of present disclosure.

In an embodiment, the medical event image 215 may be generated to represent the health status of the patient based on the corresponding medical event. Upon generating the medical event image 215 for each of the one or more medical events, the medical event image 215 for each of the one or more medical events are stitched for generating the medical image 218. FIG. 7 illustrates the generated medical image 700 comprising one or more medical event images 701.1 . . . 701.4. Consider, the textual data 208 illustrated in Table 1. The medical event image 701.1 may be generated for the medical event with the quantitative attribute of 90%. The medical event image 701.2 may be generated for the medical event with the quantitative attribute of 70%. The medical event image 701.3 may be generated for the medical event with the quantitative attribute of 45%. The medical event image 701.4 may be generated for the medical event with the quantitative attribute of 10%. The one or more medical event images 701.1 . . . 701.4 may be stitched in the predefined pattern for generating the medical image 700. In an embodiment, the predefined pattern may be based on the chronological order associated with the one or more medical events. The predefined pattern may be vary based on configuration of the stitching. FIG. 7 illustrates an exemplary predefined pattern of the one or more medical event images 701.1 . . . 701.4. In an embodiment, the one or more medical event images 701.1 . . . 701.4 may be arranged sequential pattern in one of vertical order and horizontal order.

In an embodiment, the one or more other modules, in the image generation system 101, may comprise a training module (not shown in the figure). The training module may be configured to the second machine learning model based on the plurality of reference images 210 and a predefined textual data. In an embodiment, the plurality of reference images 210 may be images associated with historic radiology examinations. For example, baseline scanned reports for angiography, CT, MRI, and ultrasound may be stored as the plurality of reference images 210 in the reference image repository 104. Scanned reports indicating progression of stenosis or vascular abnormalities in angiography, may be stored as the plurality of reference images 210 in the reference image repository 104. In an embodiment, the predefined textual data may be historic data associated one or more medical reports of one or more patients. In an embodiment, the predefined textual data may be provided by a user, manually, for the training. In an embodiment, the training module may retrieve the predefined textual data form a historic data repository comprising the historic data. In an embodiment, the other data 219 may comprise the predefined textual data which is stored in the image generation system 101.

In an embodiment, the one or more other modules, in the image generation system 101, may comprise a sharpening module (not shown in the figure). The sharpening module may be configured to sharpen the medical image 218 generated by the medical image generation module 204. In an embodiment, sharpening of the medical image 218 may include, initially, filtering the medical image 218 using a high-pass filter. By filtering, high-frequency components in the medical image 218 may be extracted, Further, for the sharpening, a scaled version of output of the high-pass filter is added to the generated medical image 218. By the proposed sharpening, a sharpened image of the medical image 218 may be obtained. In an embodiment, by sharpening proposed in the present disclosure, homogeneous regions of the medical image 218 may be kept constant and unchanged. In an embodiment, sharpening of the medical image 218 may be performed by using equation 3, given below:

$$S_{i,j} = x_{i,j} + \lambda F(x_{i,j}) \qquad (3)$$

where,

'$x_{i,j}$' may be the medical image at coordinate (i, j);

'$F(x_{i,j})$' may be function associated with the high-pass filter; and

'$\lambda$' may be a tuning parameter greater than or equal zero.

In an embodiment, value of '$\lambda$' depends on grade of sharpness desired. Increasing '$\lambda$' yields in more sharpened image. By this, higher resolution of the medical image 218 representing the one or more medical events may be obtained.

The medical image 218 may be provided to the doctor or the physician who is required to evaluate the health status of the patient. In an embodiment, the medical image 218 may be provided to the doctor or the physician upon sharpening.

The other data 219 may store data, including temporary data and temporary files, generated by modules for performing the various functions of the image generation system 101. The one or more modules 107 may also include other modules 205 to perform various miscellaneous functionalities of the image generation system 101. It will be appreciated that such modules may be represented as a single module or a combination of different modules.

Figure 3:
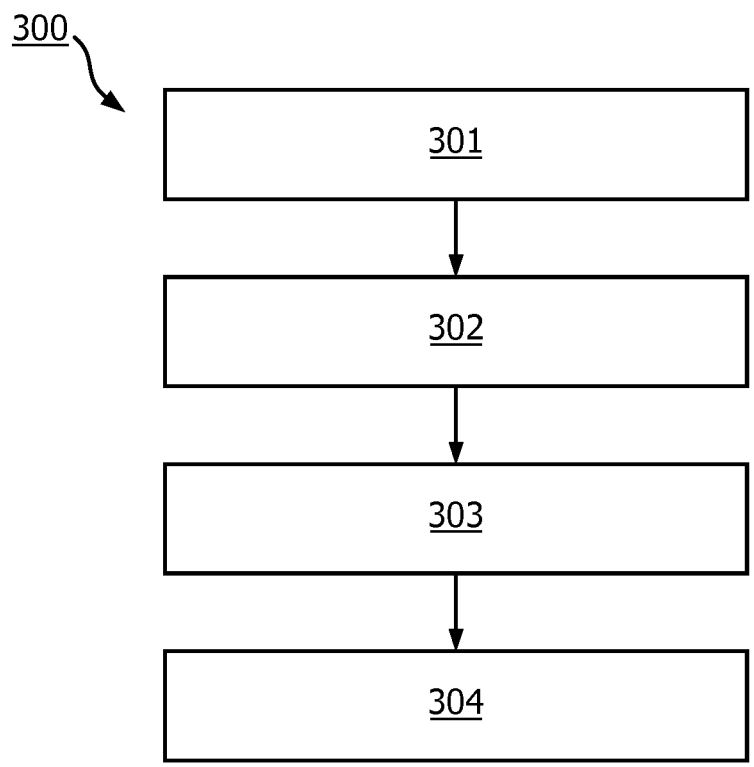
FIG. 3 illustrates a flowchart showing an exemplary method for generating a medical image based on textual data in a medical report of a patient, in accordance with some embodiments of present disclosure.

FIG. 3 illustrates a flowchart showing an exemplary method for generating the medical image 218 based on the textual data 208 in the one or more medical reports 207 of the patient, in accordance with some embodiments of present disclosure.

At block 301, the textual data retrieve module 201 may be configured to retrieve the textual data 208 from the one or more medical reports 207. The textual data 208 comprises one or more medical events and corresponding one or more attributes associated with each of the one or more medical reports 207. The one or more attributes may comprise a date attribute, a time attribute, a modality attribute, a qualitative attribute, and a quantitative attribute associated with corresponding medical event.

At block 302, based on the retrieved textual data 208, the matching score computation module 202 may be configured to compute the matching score 209 for each of plurality of reference images 210. The matching score may be computed using the second machine learning module.

Figure 4:
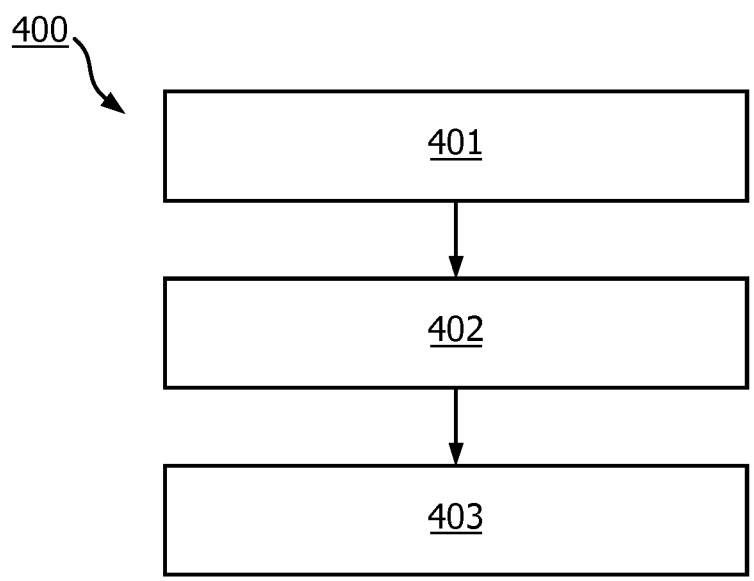
FIG. 4 illustrates a flowchart showing an exemplary method for computing matching score, in accordance with some embodiments of present disclosure.

FIG. 4 illustrates a flowchart showing an exemplary method for computing the matching score 209.

At block 401, the matching score computation module 202 may generate the vector representation 211 for each of the plurality of reference images 210. One or more techniques, known to a person skilled in the art, may be implemented for generating the vector representation 211.

At block 402, the matching score computation module 202 may generate the joint vector representation 212 for each of the plurality of reference images 210 based on the corresponding vector representation 211 and the textual data 208.

At block 403, the matching score computation module 202 may compute the matching score 209 for each of the plurality of reference images 210 based on the joint vector representation 212 of respective reference image.

Referring back to FIG. 3, at block 303, the image selection module 203 may be configured to select the one or more images from the plurality of the reference images 210. The one or more images may be selected based on the matching score 209 associated with each of the plurality of reference images 210.

Figure 5:
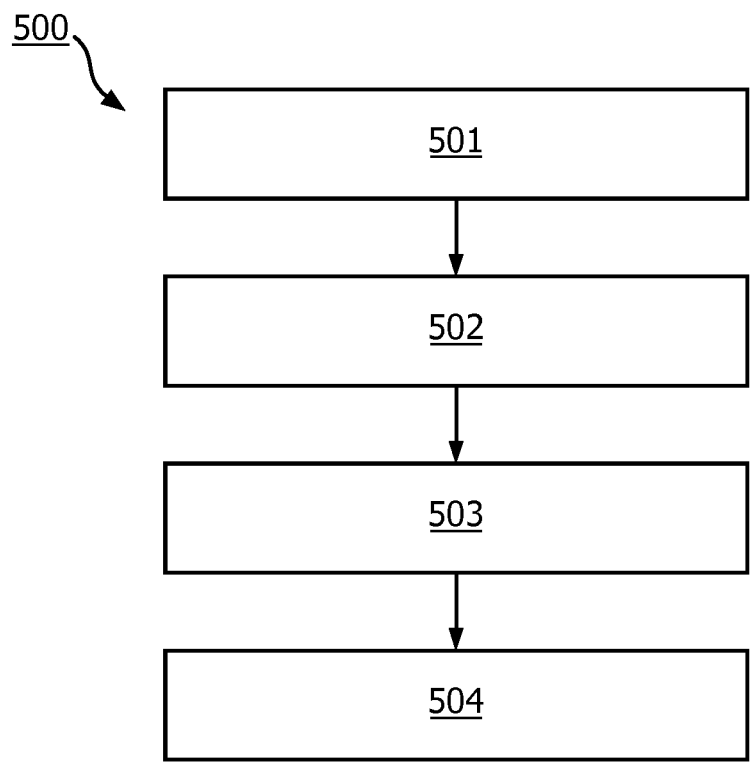
FIG. 5 illustrates a flowchart showing an exemplary method generating a medical image using a second machine learning model, in accordance with some embodiments of present disclosure.

At block 304, the medical image generation module 204 may be configured to generate the medical image 218 for the patient based on the one or more images and the textual data 208. The medical image may be generated using the second machine learning model. FIG. 5 illustrates a flowchart showing an exemplary method generating the medical image 218 using the second machine learning model.

Figure 6:
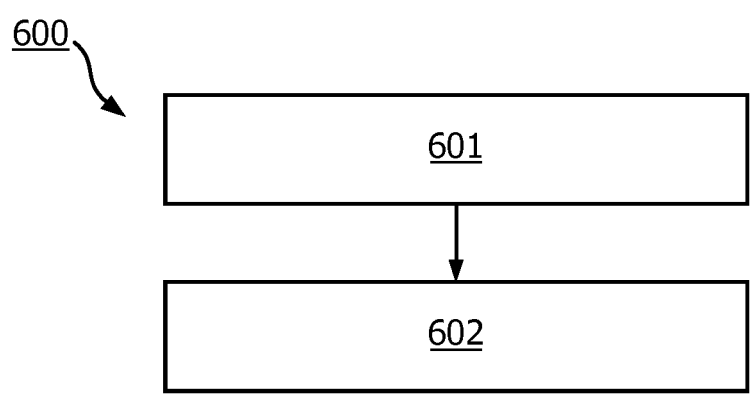
FIG. 6 illustrates a flowchart showing an exemplary method for retrieving first sequence for generating a medical image, in accordance with some embodiments of present disclosure.

At block 501, the medical image generation module 204 may retrieve the first sequence 213 comprising vector representation 211 of one of words and phrases in the textual data 208. FIG. 6 illustrates a flowchart showing an exemplary method for retrieving the first sequence 213 for generating the medical image 218.

At block 601, the medical image generation module 204 may determine the backward hidden states 216 and forward hidden states 217 associated with one of the words and the phrases in the textual data. The backward hidden states 216 and the forward hidden states 217 may be determined using backward Long Short-Term Memory (LSTM) unit and forward LSTM unit, respectively.

At block 602, the medical image generation module 204 may concatenate the backward hidden states 216 and the forward hidden states 217 for retrieving the first sequence 213.

Referring back to FIG. 5, at block 502, the medical image generation module 204 may generate the second sequence 214 comprising the one or more images selected from the plurality of reference images 210.

At block 503, the medical image generation module 204 may generate the medical event image for each of the one or more medical events of the textual data 208. The medical event image may be generated based on the first sequence 213 and the second sequence 214.

At block 504, the medical image generation module 204 may stitch the medical event image of each of the one or more medical events in the predefined pattern.

As illustrated in FIGS. 3, 4, 5 and 6 the methods 300, 400, 500 and 600 may include one or more blocks for executing processes in the image generation system 101. The methods 300, 400 and 500 may be described in the general context of computer executable instructions.

Generally, computer executable instructions can include routines, programs, objects, components, data structures, procedures, modules, and functions, which perform particular functions or implement particular abstract data types.

The order in which the methods 300, 400, 500 and 600 are described may not intended to be construed as a limitation, and any number of the described method blocks can be combined in any order to implement the method. Additionally, individual blocks may be deleted from the methods without departing from the scope of the subject matter described herein. Furthermore, the method can be implemented in any suitable hardware, software, firmware, or combination thereof.

Computing System

Figure 8:
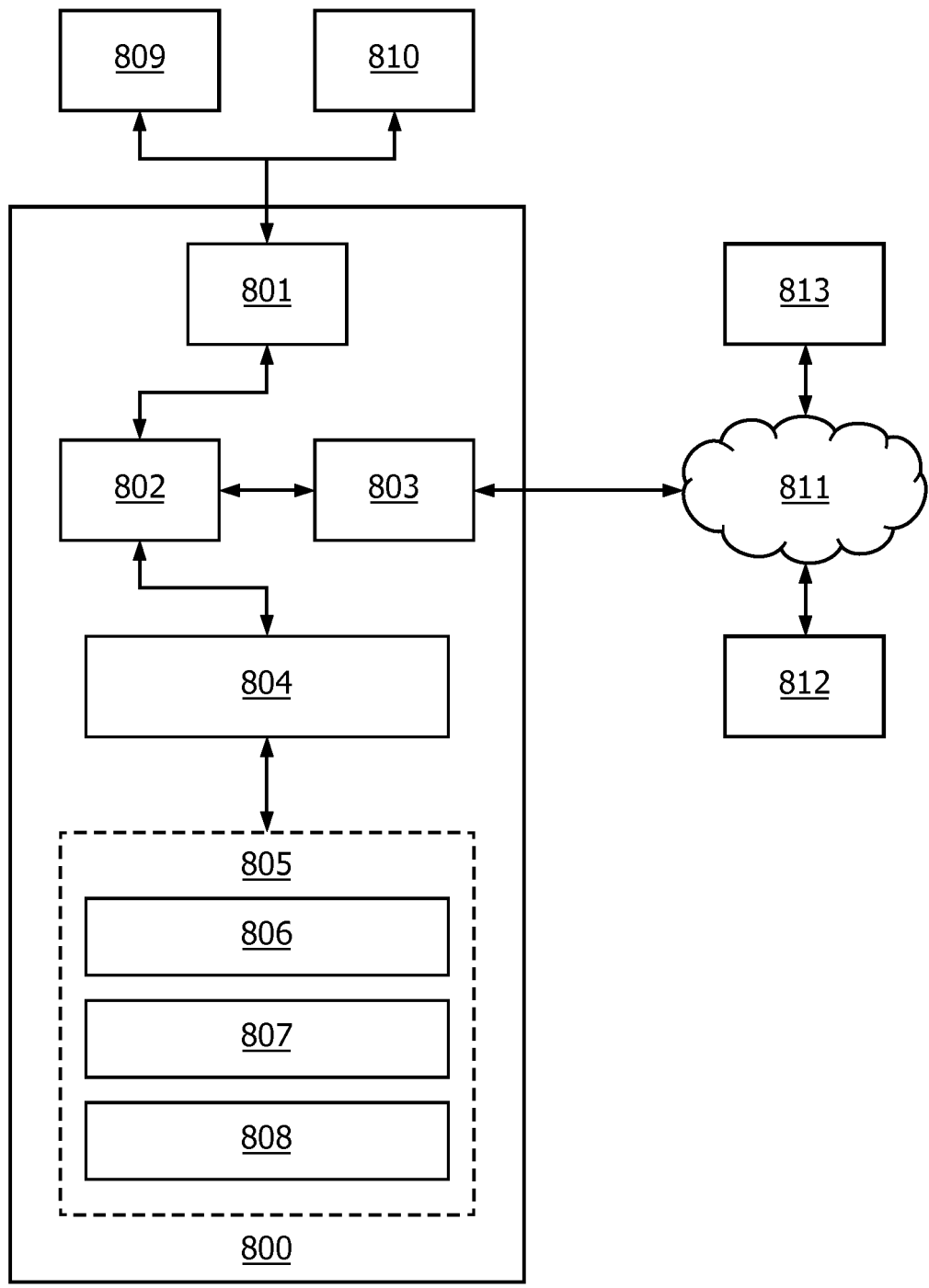
FIG. 8 illustrates a block diagram of an exemplary computer system for implementing embodiments consistent with the present disclosure.

FIG. 8 illustrates a block diagram of an exemplary computer system 800 for implementing embodiments consistent with the present disclosure. In an embodiment, the computer system 800 is used to implement the image generation system 101. The computer system 800 may include a central processing unit ("CPU" or "processor") 802. The processor 802 may include at least one data processor for executing processes in Virtual Storage Area Network. The processor 802 may include specialized processing units such as, integrated system (bus) controllers, memory management control units, floating point units, graphics processing units, digital signal processing units, etc.

The processor 802 may be disposed in communication with one or more input/output (I/O) devices 809 and 810 via I/O interface 801. The I/O interface 801 may employ communication protocols/methods such as, without limitation, audio, analog, digital, monaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 801, the computer system 800 may communicate with one or more I/O devices 809 and 810. For example, the input devices 809 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output devices 810 may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 800 may consist of the image generation system 101. The processor 802 may be disposed in communication with the communication network 811 via a network interface 803. The network interface 803 may communicate with the communication network 811. The network interface 803 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 811 may include, without limitation, a direct interconnection, local area network (LAN), wide area network (WAN), wireless network (e.g., using Wireless Application Protocol), the Internet, etc. Using the network interface 803 and the communication network 811, the computer system 800 may communicate with a medical report repository 812 and a reference image repository 813 for generating the medical image. The network interface 803 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 811 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi, and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 802 may be disposed in communication with a memory 805 (e.g., RAM, ROM, etc. not shown in FIG. 8) via a storage interface 804. The storage interface 804 may connect to memory 805 including, without limitation, memory drives, removable disc drives, etc., employing connection protocols such as, serial advanced technology attachment (SATA), Integrated Drive Electronics (IDE), IEEE-1394, Universal Serial Bus (USB), fibre channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 805 may store a collection of program or database components, including, without limitation, user interface 806, an operating system 807 etc. In some embodiments, computer system 800 may store user/application data 806, such as, the data, variables, records, etc., as described in this disclosure. Such databases may be implemented as fault-tolerant, relational, scalable, secure databases such as Oracle® or Sybase®.

The operating system 807 may facilitate resource management and operation of the computer system 800. Examples of operating systems include, without limitation, APPLE MACINTOSH® OS X, UNIX®, UNIX-like system distributions (E.G., BERKELEY SOFTWARE DISTRIBUTION™ (BSD), FREEBSD™, NETBSD™, OPENBSD™, etc.), LINUX DISTRIBUTIONS™ (E.G., RED HAT™, UBUNTU™, KUBUNTU™, etc.), IBM™ OS/2, MICROSOFT™ WINDOWS™ (XP™, VISTA™/7/8, 10 etc.), APPLE® IOS™, GOOGLE® ANDROID™, BLACKBERRY® OS, or the like.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

Advantages

An embodiment of the present disclosure eliminates the need for deployment of complex and costly medical management system by generating required medical images dynamically using available text in the medical reports.

An embodiment of the present disclosure minimizes risk of errors when doctors or physicians, in low-resource settings rely solely on available medical reports. Medical image generated in the present disclosure aids in recalling findings and makes accurate assessments on previous radiology of a patient.

An embodiment of the present disclosure facilitates better evaluation of disease progression and communication of accurate details to the patient based on visuals from generated medical image.

An embodiment of the present disclosure improve engagement and share decision-making between patients and their healthcare providers towards achieving desired health outcomes by visually depicting potential outcomes based on treatment interventions over a period of time.

An embodiment of the present disclosure provisions in understanding progression of health status of a patient over a period of time and provides a medical image indicating the progression.

An embodiment of the present disclosure facilitates regeneration of medical image at scenarios where scanned medical reports may be lost or unavailable.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media may include all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as, an optical fibre, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" includes non-transitory computer readable medium, hardware logic, and/or transmission signals in which code may be implemented. A device in which the code implementing the described embodiments of operations is encoded may include a computer readable medium or hardware logic. Of course, those skilled in the art will recognize that many modifications may be made to this configuration without departing from the scope of the invention, and that the article of manufacture may include suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIGS. 3, 4, 5 and 6 show certain events occurring in a certain order. In alternative embodiments, certain operations may be performed in a different order, modified, or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Health care system |
| 101 | Image generation system |
| 102 | Communication network |
| 103 | Medical report repository |
| 104 | Reference image repository |
| 105 | Processor |
| 106 | I/O interface |
| 107 | Modules |
| 108 | Memory |
| 201 | Textual data retrieve module |
| 202 | Matching score computation module |
| 203 | Image selection module |
| 204 | Medical image generation module |
| 205 | Other modules |
| 206 | Data |
| 207 | Medical report data |
| 208 | Textual data |
| 209 | Matching score |
| 210 | Reference image data |
| 211 | Vector representation data |
| 212 | Joint vector representation data |
| 213 | First sequence data |
| 214 | Second sequence data |
| 215 | Medical event image data |
| 216 | Backward hidden state data |
| 217 | Forward hidden state data |
| 218 | Medical image data |
| 219 | Other data |
| 700 | Medical image |
| 701.1 . . . 701.4 | Medical event images |
| 800 | Computer System |
| 801 | I/O Interface |
| 802 | Processor |
| 803 | Network Interface |
| 804 | Storage Interface |
| 805 | Memory |
| 806 | User Interface |
| 807 | Operating System |
| 808 | Web Server |
| 809 | Input Devices |
| 810 | Output Devices |
| 811 | Communication Network |
| 812 | Medical report repository |
| 813 | Reference image repository |

The invention claimed is:

1. A method for generating a medical image based on textual data in a medical report of a patient, comprising:

retrieving, by an image generation system, a textual data from each of one or more medical reports of a patient, wherein the textual data comprises one or more medical events and corresponding two or more attributes associated with each of the one or more medical reports, wherein the two or more attributes comprise a qualitative attribute indicating a medical problem associated with the patient and a quantitative attribute indicating a quantity associated with the medical problem;

computing, by the image generation system, a matching score for each of plurality of reference images based on the textual data, using a first machine learning model;

selecting, by the image generation system, one or more images from the plurality of reference images based on the matching score associated with each of the plurality of reference images, wherein each one of the one or more images selected from the plurality of reference images has a higher value of the matching score than values of the matching score for the other images from the plurality of reference images not selected; and generating, by the image generation system, one or more medical event images for the patient based on the one or more images and the one or more medical events of the textual data using a second machine learning model, wherein a medical event image of the one or more medical event images is generated for an associated medical event with the corresponding quantitative attribute indicating the quantity associated with the medical problem.

2. The method as claimed in claim 1, wherein the one or more medical events and the corresponding one or more attributes, in the textual data, are in a chronological order.

3. The method as claimed in claim 1, wherein the one or more attributes, corresponding to each of the one or more medical events in the textual data, comprises a date attribute, a time attribute, a modality attribute associated with corresponding medical event.

4. The method as claimed in claim 1, wherein computing the matching score comprises:
generating, by the image generation system, a vector representation for each of the plurality of reference images;
generating, by the image generation system, a joint vector representation for each of the plurality of reference images based on the corresponding vector representation and the textual data; and
computing, by the image generation system, the matching score for each of the plurality of reference images based on the joint vector representation of respective reference image.

5. The method as claimed in claim 1, wherein each of the one or more images selected from the plurality of reference images are associated with the matching score greater than a predefined matching score.

6. The method as claimed in claim 1, wherein generating the medical image, comprises:
retrieving, by the image generation system, a first sequence comprising vector representation of one of words and phrases in the textual data;
generating, by the image generation system, a second sequence comprising the one or more images;
generating, by the image generation system, a medical event image for each of the one or more medical events of the textual data, based on the first sequence and the second sequence; and stitching, by the image generation system, the medical event image of each of the one or more medical events in a predefined pattern, for generating the medical image.

7. The method as claimed in claim 6, wherein retrieving the first sequence comprises:
determining, by the image generation system, backward hidden states and forward hidden states associated with one of the words and the phrases in the textual data; and
concatenating, by the image generation system, the backward hidden states and the forward hidden states for retrieving the first sequence.

8. The method as claimed in claim 7, wherein the backward hidden states and the forward hidden states is determined using backward Long Short-Term Memory (LSTM) unit and forward LSTM unit, respectively.

9. The method as claimed in claim 1, wherein the second machine learning model is trained based on the plurality of reference images and a predefined textual data.

10. The method as claimed in claim 1, wherein the first machine learning model is a multimodal Convolution Neural Network (CNN) and the second machine learning model is a Recurrent Neural Network (RNN) model.

11. An image generation system for generating a medical image based on textual data in a medical report of a patient, comprises:
a processor; and
a memory communicatively coupled to the processor, wherein the memory stores processor-executable instructions, which, on execution, cause the processor to:
retrieve a textual data from each of one or more medical reports of a patient, wherein the textual data comprises one or more medical events and corresponding two or more attributes associated with each of the one or more medical reports, wherein the two or more attributes comprise a qualitative attribute indicating a medical problem associated with the patient and a quantitative attribute indicating a quantity associated with the medical problem;
compute a matching score for each of plurality of reference images based on the textual data, using a first machine learning model;
select one or more images from the plurality of reference images based on the matching score associated with each of the plurality of reference images, wherein each one of the one or more images selected from the plurality of reference images has a higher value of the matching score than values of the matching score for the other images from the plurality of reference images not selected; and
generate one or more medical images for the patient based on the one or more images and the one or more medical events of the textual data using a second machine learning model, wherein a medical event image of the one or more medical event images is generated for an associated medical event with the corresponding quantitative attribute indicating the quantity associated with the medical problem.

12. The image generation system as claimed in claim 11, wherein the one or more medical events and the corresponding one or more attributes, in the textual data, are in a chronological order.

13. The image generation system as claimed in claim 11, wherein the one or more attributes, corresponding to each of the one or more medical events in the textual data, comprises a date attribute, a time attribute, a modality attribute associated with corresponding medical event.

14. The image generation system as claimed in claim 11, wherein computing the matching score comprises:
generating a vector representation for each of the plurality of reference images;
generating a joint vector representation for each of the plurality of reference images based on the corresponding vector representation and the textual data ; and
computing the matching score for each of the plurality of reference images based on the joint vector representation of respective reference image.

15. The image generation system as claimed in claim 11, wherein each of the one or more images selected from the plurality of reference images are associated with the matching score greater than a predefined matching score.

16. The image generation system as claimed in claim 11, wherein generating the medical image, comprises:
retrieving a first sequence comprising vector representation of one of words and phrases in the textual data;
generating a second sequence comprising the one or more images;
generating a medical event image for each of the one or more medical events of the textual data, based on the first sequence and the second sequence; and
stitching the medical event image of each of the one or more medical events in a predefined pattern, for generating the medical image.

17. The image generation system as claimed in claim 16, wherein retrieving the first sequence comprises:
determining backward hidden states and forward hidden states associated with one of the words and the phrases in the textual data; and
concatenating the backward hidden states and the forward hidden states for retrieving the first sequence.

18. The image generation system as claimed in claim 17, wherein the backward hidden states and the forward hidden states is determined using backward Long Short-Term Memory (LSTM) unit and forward LSTM unit, respectively.

19. The image generation system as claimed in claim 11, wherein the second machine learning model is trained based on the plurality of reference images and a predefined textual data.

20. The image generation system as claimed in claim 11, wherein the first machine learning model is a multimodal Convolution Neural Network (CNN) and the second machine learning model is a Recurrent Neural Network (RNN) model.

\* \* \* \* \*